United States Patent [19]

Szita et al.

[11] Patent Number: 5,451,638
[45] Date of Patent: Sep. 19, 1995

[54] COPOLYMERIC AMINOPLAST CROSSLINKING AGENTS

[75] Inventors: Jeno G. Szita, Norwalk; Robert G. Lees, Stamford, both of Conn.

[73] Assignee: Cytec Technology Corp., Wilmington, Del.

[21] Appl. No.: 213,312

[22] Filed: Mar. 14, 1994

Related U.S. Application Data

[63] Continuation-in-part of Ser. No. 58,085, May 10, 1993, abandoned.

[51] Int. Cl.$^6$ ............................................. C08F 26/06
[52] U.S. Cl. ................................. 525/176; 526/259; 526/261; 526/302; 525/182; 525/204; 525/210; 525/326.8; 544/197
[58] Field of Search ............... 526/259, 261, 302; 525/176, 182, 204, 210, 326.8; 544/197

[56] References Cited

U.S. PATENT DOCUMENTS

| | | | |
|---|---|---|---|
| 3,290,350 | 12/1966 | Hoover | 560/113 |
| 4,130,577 | 12/1978 | Nagato et al. | 560/379 |
| 4,377,530 | 3/1983 | Trenbeath et al. | 560/377 |
| 4,439,616 | 3/1984 | Singh et al. | 560/25 |
| 4,853,478 | 8/1989 | Colvin et al. | 526/301 |
| 5,071,938 | 12/1991 | Halpaap et al. | 528/45 |
| 5,294,671 | 3/1994 | Szita et al. | 525/187 |

OTHER PUBLICATIONS

Abstract of German Patent No. 4,120,323, published Dec. 12, 1992.

*Primary Examiner*—Melvyn I. Marquis
*Assistant Examiner*—R. F. Johnson
*Attorney, Agent, or Firm*—Bart E. Lerman; Michael J. Kelly; Claire M. Schultz

[57] ABSTRACT

A copolymer of a TMI/amino compound 1:1 monoadduct with ethylenically unsaturated comonomers is provided, as well as a process for producing the same. Such copolymers in and of themselves may find use as aminoplast crosslinking agents, or can readily be modified thereto. Curable compositions can be formulated from the crosslinker alone or in combination with polyfunctional active hydrogen compounds, which can be cured to produce crosslinked films and objects.

29 Claims, No Drawings

COPOLYMERIC AMINOPLAST CROSSLINKING AGENTS

This is a continuation-in-part of application Ser. No. 08/058,085, filed May 10, 1993, now abandoned, which is incorporated by reference herein as if fully set forth.

BACKGROUND OF THE INVENTION

1. Field of the Invention

This invention relates generally to a novel class of functional copolymers and derivatives thereof which can be used as aminoplast crosslinking agents in a variety of fields, and particularly in the coating field.

2. Description of the Related Art

To effectively crosslink with a variety of widely available difunctional materials such as diols, dicarboxylic acids, dimercaptans, and diamides, a monomeric crosslinking agent is required to have a functionality effective for crosslinking of greater than two, and preferably at least 3. In many cases, however, even trifunctional aminoplast crosslinking agents do not give rise to sufficient crosslinking density in cured films or objects due to incomplete reaction of the functional groups, and as a result, cured films with inferior physical and resistance properties are obtained.

The problem of insufficient crosslinking density may be overcome by using a higher functional aminoplast crosslinker such as hexamethoxymethyl melamine. In these cases, however, the films obtained sometimes have low flexibility due to the somewhat rigid network produced in the films upon cure.

The above-identified problems of insufficient crosslinking of the low functionality crosslinkers and the low flexibility of the highly functional crosslinkers may be overcome by using typically tetrafunctional guanamine-derived aminoplast crosslinking agents. However, guanamine-derived crosslinkers are more difficult and more costly to prepare than melamine-derived crosslinkers. Furthermore, some guanamine crosslinkers such as N,N,N',N'-tetraalkoxymethylbenzoguanamines may have insufficient resistance properties for certain applications, and generally have inferior stability towards the degradative action of ultraviolet light.

The present invention, therefore, provides new polyfunctional, amino resin derived, copolymeric crosslinking agents which are capable of self crosslinking or crosslinking with active hydrogen containing materials thereby producing, upon cure, films which have good acid resistance properties, environmental etch resistance, and a good balance of hardness and flexibility.

SUMMARY OF THE INVENTION

In its overall aspect, the present invention provides a novel highly functional copolymer which can function as an effective aminoplast crosslinking agent, or from which effective aminoplast crosslinking agents can be derived. More specifically, the copolymers of the present invention comprise repeating units derived from (i) a monoadduct of an isopropenyl-alpha, alpha-dimethylbenzyl isocyanate and an amino compound; and (ii) an ethylenically unsaturated compound capable of copolymerizing with said monoadduct. The aminoplast crosslinking agents in accordance with the present invention are the alkylolated and/or alkoxyalkylated derivatives of these copolymers.

In general, the present copolymers are prepared by the copolymerization of (1) an unsaturated monoadduct of an amino compound and isopropenyl-alpha,alpha-dimethylbenzyl isocyanate ("TMI"), with (2) a suitable unsaturated comonomer. The crosslinking agents are the alkylolated and, optionally, etherified versions of the copolymer, which may be accomplished prior or subsequent to the aforementioned copolymerization.

The present invention also provides a curable composition comprising the copolymeric aminoplast crosslinking agent and, optionally, an active hydrogen group-containing resin, as well as a method of coating using this curable composition and a cured film or object prepared thereby.

These and other features and advantages of the present invention will be more readily understood by those skilled in the art from a reading of the following detailed description.

DETAILED DESCRIPTION OF THE PREFERRED EMBODIMENTS

As indicated above, the copolymeric aminoplast crosslinking agent of the present invention is a partially or fully alkylolated and/or alkoxyalkylated, preferably a partially or fully methylolated and/or alkoxymethylated, copolymer of a TMI/amino compound monoadduct and an ethylenically unsaturated compound capable of copolymerizing therewith.

As utilized herein, the term "amino compound" refers non-polymeric nitrogen containing compounds and derivatives thereof which are commonly utilized as crosslinking agents in coatings application. In general, such amino compounds are well-known to those of ordinary skill in the art and include, most commonly, melamines, guanamines such as benzo-, aceto-, and cyclohexylcarbo- guanamines, glycolurils and ureas, as well as the at least partially N-alkylolated and N-alkoxyalkylated derivatives thereof. The term "amino compound" also includes the oligomers of such amino compounds.

As suitable melamine and melamine derivatives (collectively referred to as melamines) may be mentioned those of the following general formula

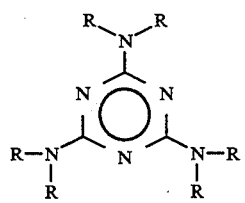

wherein each R is independently selected from H, an alkylol group and an alkoxyalkyl group. Preferred melamines are those wherein each R is independently selected from H, a methylol group and an alkoxymethyl group having from 1 to 6 carbon atoms in the alkoxy group.

As suitable guanamines and guanamine derivatives (collectively referred to as guanamines) may be mentioned those of the following general formula

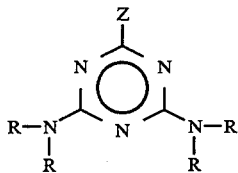

wherein Z is selected from H, an alkyl group of from 1 to 20 carbon atoms, an aryl group of from 6 to 20 carbon atoms, and an aralkyl group of from 7 to 20 carbon atoms, and wherein each R is independently selected from H, an alkylol group and an alkoxyalkyl group. Preferred guanamines are those wherein each R is independently selected from H, a methylol group and an alkoxymethyl group having from 1 to 6 carbon atoms in the alkoxy group, and particularly wherein Z is selected from a phenyl group (benzoguanamines), a methyl group (acetoguanamines) and a cyclohexyl group (cyclohexylcarboguanamines).

As suitable glycolurils and glycoluril derivatives (collectively referred to as glycolurils) may be mentioned those of the following general formula

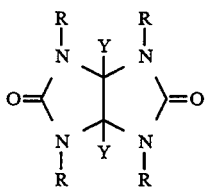

wherein Y is selected from H, an alkyl group of from 1 to 20 carbon atoms, an aryl group of from 6 to 20 carbon atoms, and an aralkyl group of from 7 to 20 carbon atoms, and wherein each R is independently selected from H, an alkylol group and an alkoxyalkyl group. Preferred glycolurils are those wherein each R is independently selected from H, a methylol group and an alkoxymethyl group having from 1 to 6 carbon atoms in the alkoxy group, and particularly wherein Y is selected from H and a methyl group.

As suitable ureas and urea derivatives (collectively referred to as ureas) may be mentioned those of the following general formula

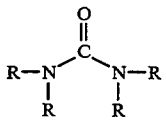

wherein each R is independently selected from H, an alkylol group and an alkoxyalkyl group. Preferred ureas are those wherein each R is independently selected from H, a methylol group and an alkoxymethyl group having from 1 to 6 carbon atoms in the alkoxy group.

The TMI/amino compound monoadduct may be prepared by contacting TMI with an amino compound or a mixture of amino compounds. TMI, or isopropenyl-alpha, alpha-dimethylbenzyl isocyanate, has the following general formula

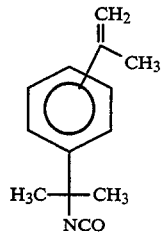

Preferred is the meta-isomer (m-TMI), the para-isomer (p-TMI), or a mixture of the meta- and para- isomers (m/p-TMI). The meta- isomer is available commercially from Cytec Industries Inc., West Paterson, N.J., under the trade name TMI ® (meta) Unsaturated Aliphatic Isocyanate. The para- isomer may be prepared by procedures described in U.S. Pat. Nos. 3,290,350, 4,130,577, 4,377,530 and 4,439,616, all of which are incorporated herein by reference as if fully set forth.

The preparation of a TMI/melamine adduct is disclosed in the commonly owned, U.S. application Ser. No. 08/060,135, filed 13 May 1993,now U.S. Pat. No. 5,294,671, which is incorporated by reference herein as if fully set forth. The TMI/amino compound monoadducts of amino compounds other than melamine can be produced in a substantially identical manner.

Generally, the TMI/amino compound adduct may be prepared by contacting TMI with the amino compound in a solvent having a high boiling point, a high dipole moment, and a high dielectric constant, at a temperature and for a length of time to produce a 1:1 adduct. The adduct is then isolated by cooling the reaction mixture and filtering the precipitated adduct. The adduct thus obtained is substantially monomeric (monounsaturated functional) and is suitable for use as the starting monomer in the preparation of copolymer intermediates from which the copolymeric aminoplasts of the invention are prepared.

Preferably, the monoadduct of TMI and the amino compound is prepared using a substantially stoichiometric (about 1:1) molar ratio of the TMI to amino compound, which is normally preferred on the basis of reaction stoichiometry. However, the adduct-forming reaction may be carried out at any ratio. For example, if a TMI to amino compound molar ratio of 0.5:1 is used, there will remain a large excess of unreacted amino compound which may be separated from the product, which product is necessarily a 1:1 adduct. If, on the other hand, excess quantities of TMI such as a 5:1 molar excess are used, only the monoaddition product is obtained under the process conditions described herein. The unreacted TMI in this case may be easily removed by precipitation of the product.

It is preferred to utilize an amino compound wherein at least one R group is H, more preferably wherein both R groups on at least one pendant nitrogen are H, and preferably wherein all R groups are H.

The preferred solvents for the reaction are aprotic solvents having relatively high boiling points, high dipole moments, and high dielectric constants for facilitating the dissolution of the more sparingly soluble amino compounds at the reaction temperature and for allowing the product to crystallize at ambient temperatures. The preferred solvent is dimethylsulfoxide; however, solvents such as N,N-dimethylformamide, N,N-dimethylacetamide, N-methylpyrrolidone, sulfolane, hexamethylphosphorus triamide (HMPT), hexamethylphosphoramide (HMPA), and mixtures thereof may also be used. Any solvent to reactant ratio may be used to prepare the TMI/amino compound monoadducts. The preferred range of the solvent to reactant ratio is from about 1:1 to about 3:1. Most preferably, the ratio is about 2:1.

The preferred temperature for carrying out the monaddition reaction is in the range from about 80° C. to about 150° C. At temperatures lower than about 80° C., the reaction proceeds at a very slow rate. At temperatures higher than about 150° C., side reactions, including decomposition of the solvent and TMI reactant, may become significant. A temperature in the range of about 100° C. to about 120° C. is most convenient to prepare the TMI/amino compound monoadduct.

The preferred time for carrying out the monoaddition reaction is in the range of from about 12 minutes to about 28 hours depending, of course, on the other reaction components and conditions. Assuming that a stoichiometric or less than stoichiometric amount of TMI is utilized, then it is preferred to continue the reaction until substantially all of the available isocyanate groups have been consumed.

After the monoaddition reaction, the monoadduct may be isolated by cooling the reaction mixture and filtering the precipitated product. The product may be further purified by washing it with an organic solvent capable of dissolving the solvent used in the process of the invention. An example of a solvent usable for this purpose is tetrahydrofuran.

Other reaction details may be had be referring to the aforementioned incorporated U.S. Pat. No. 5,294,671.

The preferred TMI/amino compound monoadducts thus prepared may be represented by the following general formula:

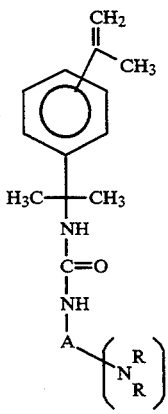

wherein A is the amino compound core, R is as defined above, and n is dependent upon the particular type of amino compound. For example, if the amino compound is melamine, then A is a 1,3,5-triazine core, all of the R groups are H and n is 2. If the amino compound is benzoguanamine, then A is a 2-phenyl-1,3,5-triazine core, all R groups are H and n is 1.

The copolymers of the present invention comprise repeating units derived from (i) the aforementioned monoadduct and (ii) an ethylenically unsaturated compound capable of copolymerizing with such monoadduct.

The ethylenically unsaturated comonomers from which the copolymeric aminoplasts of the invention may be prepared are comonomers represented by the formula:

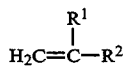

wherein $R^1$ and $R^2$ are the same or different and are independently selected from the group consisting of hydrogen, cyano, halo such as chloro, alkoxy, acetoxy, acyl, aminocarbonyl, N-alkylaminocarbonyl, N,N-dialkyl-aminocarbonyl, aryl, alkoxycarbonyl of 1 to 20 carbon atoms, aryloxycarbonyl of 6 to 20 carbon atoms, and aralkyloxycarbonyl of 7 to 20 carbon atoms.

Suitable comonomers include without limitation, the following classes of monosubstituted and vicinally or geminally disubstituted unsaturated compounds: vinylidenes, vinyl halides, vinylidene halides, vinyl carboxylates, vinyl ethers, alpha, beta-unsaturated aldehydes and ketones, styrenes, alpha-methyl styrenes, fumarate and maleate esters, acrylic and methacrylic acid amides, acrylic and methacrylic nitriles, and acrylic and methacrylic esters. Suitable comonomers include the following unsaturated compounds: methylene valerolactone, vinyl chloride, vinylidene chloride, vinyl acetate, hexyl vinyl ether, methyl vinyl ketone, maleimide, N-substituted maleimides, acrolein, styrene, alpha-methylstyrene, para-methyl styrene, acrylamide, methacrylamide, acrylonitrile, methacrylonitrile, dimethyl fumarate, dimethyl maleate, maleic anhydride, methyl acrylate, methyl methacrylate, ethyl acrylate, butyl acrylate, butyl methacrylate, ethylhexyl acrylate, ethylhexyl methacrylate, beta-hydroxyethyl acrylate, beta-hydroxyethyl methacrylate and beta- and gamma- hydroxypropyl acrylate and methacrylate.

Preferred of the above may be mentioned the following:

A. monosubstituted olefins such as acrylate esters illustrative of which are methyl acrylate and butyl acrylate; vinyl nitriles such as acrylonitrile; vinyl carboxylates such as vinyl acetate; vinyl halides such as vinyl chloride; aromatic olefins such as styrerie; acrylic amides such as acrylamide; and the like;

B. 1,1- disubstituted olefins such as methacrylate esters illustrative of which are methyl methacrylate and butyl methacrylate; methacrylic amides such as methacrylamide; methacrylonitrile; vinylidene chloride; and the like;

C. 1,2- disubstituted olefins such as dialkyl esters of fumaric and maleic acids, esters of cinnamic acids, maleic arthydride, maleimide, N-methyl maleimide, N-phenyl maleimide, and the like; and D. more highly substituted olefins which are sufficiently reactive to undergo copolymerization with the monoadduct.

The mono- and disubstituted olefins and mixtures thereof are especially preferred. Particularly preferred of these are acrylate and methacrylate esters derived from alcohols of 1 to 20 carbon atoms. Most preferred are acrylate and methacrylate esters derived from 1 to 8 carbon alcohols, and especially butyl acrylate and methyl methacrylate.

The copolymer in accordance with the present invention can be prepared by well-known procedures for polymerizing ethylenically unsaturated components. Preferably, such copolymers are prepared by the steps of:

(a) dissolving, in a liquid medium, the aforementioned TMI/amino compound monoadduct;
(b) adding to said monoadduct solution (i) an unsaturated comonomer, and (ii) a free radical initiator; and
(c) maintaining the reaction mixture at a temperature and for a length of time sufficient to copolymerize at least 90 weight percent of the adduct and the comonomer reactants.

The liquid medium in step (a) usable in the reactor charge is typically a solvent selected from the group consisting of alcohols, ketones, ethers, esters, aromatic hydrocarbons, halogenated hydrocarbons, N-methyl pyrrolidone, N,N-dimethylformamide, N,N-dimethylacetamide, and mixtures thereof. Of these solvents, N-methyl pyrrolidone is preferred.

A chain transfer agent may be optionally added to the monoadduct to limit molecular weights, which is typically a mercaptan and is selected from a group consisting of dodecyl mercaptan, butyl mercaptan, mercaptoacetic acid, and 2-mercapto-ethanol. Dodecyl mercaptans are preferred. The 2-mercaptoethanol chain transfer agent is particularly preferred in cases where hydroxy-terminated copolymers are desirable. The concentration of the chain transfer agent in the reactor charge is typically from about 0.001 to about 10 weight percent.

The free radical initiator (ii) in the reactor charge is selected from the group consisting of peresters, alkyl peroxides, acyl peroxides, percarbonates, and azobisnitriles. Of these, peresters are preferred, tertiary butyl peroctoate and tertiary amylperoctoate being the most preferred free radical initiators. The addition of ingredients (i) and (ii) in step (b) may be carried out sequentially or simultaneously, as desired, to control the molecular weight and the composition of the polymer.

The molecular weight of the polymer can be further controlled by controlling the radical initiator and chain transfer agent concentrations such that, when lower levels of either or both are employed, higher molecular weight polymers are obtained. In an opposite sense, when lower molecular weight polymers are desired, higher levels of either or both reagents are used. The molecular weight may be further controlled by varying the temperature and the monomer concentrations.

The temperature of the reaction zone in steps (b) and (c) is preferably from about 50° C. to about 150° C. Selection of a specific temperature depends on the half-life, at said selected temperature, of the free radical initiator chosen for the process. In the preferred peroctoate initiator case, a temperature of 125° C. to 130° C. is preferred.

The polymerization time, in itself, is not critical, and may vary from about 30 minutes to as much as 24 hours. It is preferred, however, to allow sufficient time to polymerize at least 90 weight percent, and preferably more than 95 weight percent of the monomer and comonomers of the reaction charge.

The ratio of the monomer to comonomer in the reactor charge depends on the composition desired for the copolymer intermediate. To prepare the preferred low molecular weight copolymer intermediates of this invention, a monomer/comonomer ratio of from about 0.01:1 to about 1:1 is preferred.

The concentration of the liquid medium in step (c) in the reactor charge is preferably from about 20 weight percent to about 80 weight percent, and the ratio of the liquid medium to total remaining ingredients of the reactor charge is preferably from about 0.25 to about 4.0.

The preferred copolymers so produced as described above comprise a plurality of the same or different segments represented by the following formula:

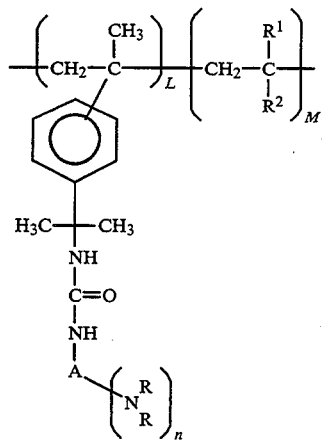

wherein L and M are the same or different integers, each independently having a value of at least 1, and wherein each R, $R^1$ and $R^2$ is as defined above.

The preferred copolymers of the invention have a molecular weight (weight average) in the range of from about 500 to about 20,000, although higher molecular weights are also usable.

The copolymers produced as described above may in and of themselves function as crosslinking agents when at least a portion of the R groups thereof are selected from alkylol and alkoxyalkyl groups, and preferably from methylol and alkoxymethyl groups containing from 1 to 6 carbon atoms in the alkoxy group. Especially preferred is the case wherein substantially all of the R groups are alkoxymethyl groups having from 1 to 6 carbon atoms in the alkoxy group, for example, methyloxymethyl, ethyloxymethyl, 1-propyloxymethyl, 2-propyloxymethyl, 1-butyloxymethyl, 2-butyloxymethyl, isobutyloxymethyl, 1-pentyloxymethyl, 1-hexyloxymethyl and cyclohexyloxymethyl.

In the event that the copolymers contain no such alkylol or alkoxyalkyl groups (all R groups are H), or insufficient R substitution to effectively function as a crosslinking agent, then the remaining =NH (R=H) groups can readily be converted via procedures well-known in the field of aminoplast crosslinkers.

Preferably, the copolymer is hydroxymethylated (or methylolated) with 1 to 30 moles, and preferably 1 to 20 moles, of formaldehyde per mole of the monoadduct added in the reaction mixture, typically in water or an alcohol, or in a mixture of water and an alcohol such as normal butanol (n-butanol). The methylolation is typically carried out under basic conditions, such as at pH 7.5 to 10, although acidic conditions may also be employed. The methylolated product thus obtained may be used as such as a crosslinking agent or may be etherified with an alcohol, and preferably with a 1 to 6 carbon alcohol under acidic conditions, typically at a pH range from about 0.5 to 6.0, and preferably from about 2 to about 4. The alcohol used to etherify the hydroxymethylated copolymeric aminoplast is usually used in a large excess to ensure a high degree of etherification and also to avoid self-crosslinking during the etherification. Therefore, the alcohol used for etherification typically is the reaction solvent.

When a mixed alkoxymethylated aminoplast is desirable, a mixture of alcohols may be used both as reactant and as solvent. The preferred alcohols are methanol, ethanol, 1-propanol, 2-propanol, 1-butanol, 2-butanol, isobutanol, 1-pentanol, 1-hexanol, cyclohexanol, and mixtures thereof.

The copolymeric aminoplast crosslinking agent of the invention may be further purified or may be used in the unpurified state. Furthermore, the reaction product may be concentrated by removing volatiles by evaporation or distillation to achieve a desired solids level or viscosity.

The novel copolymeric aminoplast crosslinking agents of the invention may be used as crosslinking agents in curable compositions to produce, upon curing, crosslinked films or objects useful in coatings, adhesives, conventional moldings, reactive injection moldings, composites, binders and others. They may also be used by themselves as self-crosslinking film formers.

The curable compositions of the present invention comprise a copolymeric aminoplast crosslinking agent as described above. Depending upon the ultimate use of such curable compositions, they may also contain one or more of a polyfunctional active hydrogen-containing material, a cure catalyst, and other additives well-known for the desired end use.

When no polyfunctional active hydrogen-containing material is present, the curable composition is a self-curing system, and when cured with or without an acid catalyst, it produces cured or crosslinked films or objects with good physical properties, as exemplified herein below in Example 4.

The polyfunctional materials usable in the invention are polyfunctional active hydrogen-containing materials including, for example, polymercaptans, polycarboxylic acids, polyamines, polyamides, epoxy or urethane prepolymers, alkyds, and polyols such as acrylic resins containing pendant or terminal functionalities, polyester resins with pendant or terminal functionalities and polyhydric alcohols. These are described in greater detail below.

The polyfunctional materials or resins used in the compositions of the invention have a molecular weight (weight average) of from about 60 to about 500,000 and comprise at least one class of an active hydrogen functionality selected from the group consisting of hydroxy, carboxy, amido, mercapto, and a group convertible thereto.

Preferred are the hydroxyfunctional polyfunctional materials having molecular weights in the range of from about 500 to about 50,000, and hydroxyl group equivalent weights of from about 200 to about 4,000. Low molecular weight multi-functional compounds such as diols, triols, etc., may also be used.

An example of a suitable polyfunctional polyester resin usable in the curable compositions of this invention is OXYESTER® Z 1439 Branched Polyester Resin, a product of Chemische Werke Hüls AG, Germany, having the following physical and chemical properties:
Hydroxyl Content (% by weight): 2
Hydroxyl Number: 65
Equivalent Weight: 863
Solids Content (% by weight): 50

Another example of a suitable polyfunctional polyester resin particularly suited for use in coil coatings is CYPLEX® 1531 modified Polyester Resin, a product of Cytec Industries Inc., West Paterson, N.J., having the following physical and chemical properties:
Solids (Weight %): 60
(Volume %): 52.9
Color (Gardner 1963): 6 (max.)
Viscosity (Gardner-Holt, 25° C.): $Y-Z_2$
Hydroxyl Number (solids): 30
Equivalent Weight (solids): 1,870
Molecular Weight, approximate: 4,000
Acid number (solids): 10 (max.)
Solvesso 150 Aromatic Hydrocarbon Solvent (%) (a product of Humble Oil and Refining Company): 40

Another example of a suitable polyfunctional resin for coil coating is CYPLEX® 1538 Modified Polyester Resin, a product of Cytec Industries Inc., West Paterson, N.J., having the following properties:
Solids (Weight %): 65
(Volume %): 58
Color (Gardner 1963): 6 (max.)
Viscosity (Gardner-Holt, 25° C.): $Z_1-Z_3$
Hydroxyl Number (solids): 40
Equivalent Weight (solids): 1,400
Molecular Weight, approximate: 2,800
Acid number (solids): 10 (max.)
Solvesso 150 Aromatic Hydrocarbon Solvent (%): 35

Another example of a suitable polyfunctional resin particularly suited to coil coatings is CYPLEX® 1546 Oil-Free Polyester Resin, a product of Cytec Industries Inc., West Paterson, N.J., having the following properties:
Non-Volatiles (weight %): 70±2
Color (Gardner 1963, max.): 4
Viscosity (Gardner-Holt, 25° C.): $Z_1-Z_3$
Acid Number (resin solids, max): 10
Hydroxyl Number (resin solids): 35–40
Equivalent Weight: 1,400–1600

An example of a suitable acrylic resin for non-coil coating application is JONCRYL® 500 Acrylic Resin, a product of S.C. Johnson and Son, Inc., Racine, Wis., having the following properties:
Solids Content (Weight %): 80
Viscosity at Room Temperature (Centipoise): 4,000
Hydroxyl Number (based on solids): 140
Equivalent Weight (based on solids): 400
Molecular Weight (Mn)*: 1,300
Polydispersity (Mw/Mn)**: 1.7
*Mn=Number Average Molecular Weight
**Mw=Weight Average Molecular Weight ARAKOTE® 3109 Hydroxy-Terminated Polyester Resin, a product of Ciba-Geigy Corporation, Hawthorne, N.Y., is an example of a solid polyester resin particularly suitable to powder coating, and has the following physical and chemical properties:
Hydroxyl Number: 27–32
Equivalent Weight: 1,900
Tg (Glass Transition, °C.): 66
ICI Viscosity at 200° C. (Poise): 40
Appearance: Colorless Solid JONCRYL® SCX-800 A Acrylic Resin and JONCRYL® SCX-800 B Acrylic Resin, products of S. C. Johnson and Son, Inc., examples of solid acrylic resins, also are suitable for powder coatings, and have the following physical and chemical properties:

|  | SCX-800A | SCX-800B |
|---|---|---|
| Non-Volatiles (Weight %): | 98 | 97 |

|                              | SCX-800A | SCX-800B |
| ---------------------------- | -------- | -------- |
| Hydroxyl Number:             | 43       | 40       |
| Equivalent Weight:           | 1300     | 1402     |
| Acid Value (mg KOH/g):       | 15       | 15–20    |
| Tg (Glass Transition, °C.):  | 43       | 43       |
| Softening Point (°C.):       | 100      | 107      |
| ICI Viscosity at 200° C. (Poise): | 25  | 45–50    |

In addition to the examples cited above, a variety of commercial polyester, acrylic, and polyurethane resins may be used as the polyfunctional ingredient of the invention, provided such resins have suitable chemical and physical properties similar to those set forth above for the polyfunctional materials.

The weight ratio of the crosslinker to polyfunctional material is from about 3:1 to about 1:40, and preferably the ratio is from about 1:1 to about 1:5. Generally, the weight percent of the crosslinker in the curable composition is from about 2.5 to about 75.

Optionally, the curable compositions of the invention may comprise cure catalysts to accelerate the curing process at a given temperature, or reduce the cure temperature at a given cure time. The catalyst, if present, is typically an acid selected from the group consisting of sulfonic, carboxylic, phosphoric, sulfuric, and nitric acids. The preferred acid catalysts are sulfonic acids, including benzenesulfonic acid, para-toluenesulfonic acid, naphthalenesulfonic acid, dinonylnaphthalenedisulfonic acid, dodecylbenzenesulfonic acid, methanesulfonic acid, and mixtures thereof. The weight ratio of the catalyst, when present, to the crosslinker in the curable composition is from about 1:4 to about 1:1,000, and the weight percent of catalyst in the curable composition is from about 0.01 to about 5.

The curable composition of the invention may optionally contain a liquid medium, which liquid medium may be used to aid the uniform application and transport of the curable composition. Any or all of the ingredients of the composition may be contacted with the liquid medium. Moreover, the liquid medium may permit formation of a dispersion, suspension, emulsion, invert emulsion, or solution of the curable composition ingredients, including other optional ingredients.

Particularly preferred is a liquid medium which is a solvent or a diluent for the curable composition ingredients. The preferred solvent or diluent is selected from the group consisting of water, alcohols, ketones, ethers, esters, aliphatic hydrocarbons, aromatic hydrocarbons, halogenated hydrocarbons, and mixtures thereof.

The weight percent of the optional liquid medium ranges from zero to about 80 and the weight ratio of the liquid medium to the total weight of the ingredients of the composition ranges from about 0.001 to about 4.

Other optional ingredients include fillers, pigments, flow control agents, anticratering additives, antioxidants, stabilizing alcohols, ultraviolet light stabilizers, plasticizers, pigment wetting additives, levelling additives, mar-proofers, mold release agents, and corrosion inhibitors.

The curable compositions may be used to prepare coatings such as solution coatings, powder coatings, coil coatings, electrodeposition coatings, and the like. They may also be used as adhesives or molding compounds.

The curable compositions may be applied onto any one of a number of well-known substrates by spraying, padding, brushing, rollercoating, curtaincoating, flowcoating, electrocoating, dipping or electrostatic spraying. The applied curable composition is thereafter cured, typically at elevated temperatures, and preferably at a temperature in the range of from about 80° C. to about 160° C. within a period of, typically, 5 minutes to 1 hour to produce crosslinked films or objects.

The foregoing general discussion of this invention will be further exemplified by the following specific examples offered by way of illustration and not limitation thereof.

EXAMPLE 1

Preparation of m-TMI/Melamine 1:1 Adduct

In a 2 liter three neck glass reactor equipped with agitator, thermometer, reflux condenser, nitrogen inlet and dropping funnel, 252 g (2 moles) of melamine was dispersed in 800 ml of DMSO (dimethylsulfoxide) under vigorous agitation. A solution of 423 g (2.1 moles) of m-TMI in 200 ml DMSO was added to the slurry at 110°–113° C. in 3.5 hours. The reaction temperature was maintained for an additional hour. To maintain effective agitation, the thickening slurry was diluted several times during the reaction with a total of 150 ml of DMSO. After cooling to ambient temperature, the reaction mixture was filtered, the white solid was rinsed on a filter with THF (tetrahydrofuran) and reslurried in 800 ml of THF. After agitation at 64° C. for 80 minutes, the product was filtered, rinsed on the filter with THF and dried first in a hot air circulation oven at 60° C. overnight (16 hours), then in a vacuum oven (full pump vacuum) at 90°–100° C. for 4 hours. The yield of the white solid product was 665 g. From the first flitrate 85 g and from the second (wash) 73 g of white solids were recovered. Infrared (IR) and Thermal Gravimetric Analysis (TGA) indicated that these products still contained 15–20% of DMSO.

The main product was characterized by NMR (Nuclear Magnetic Resonance), IR and thermal analysis. It was practically insoluble in most organic solvents, sparingly soluble in aprotic solvents such as DMSO, N-methyl-pyrrolidone, DMF (dimethylformamide), etc. Both carbon and proton NMR, as well as the IR spectra were consistent with a 1:1 adduct structure. TGA indicated about a 20% weight loss in the range of 100°–125° C. (DMSO). Major weight loss was observed above 245° C. Major thermal event by DSC (differential scanning calorimetry) was an endotherm occurring in the temperature range in which the major weight loss is observed by TGA (extrap. onset: 223° C.). Liquidification was observed by TM (Thermal Microscopy) in the same range (onset 232° C.) and "boiling" started at 248° C.

EXAMPLE 2

Copolymerization of m-TMI/Melamine Adduct

A glass reactor equipped with thermometer, stirrer, nitrogen inlet, dropping funnel and reflux condenser was charged with 16.4 g (0.05 moles) of the adduct of Example 1 and 40 g of N-methyl pyrrolidone. On heating the slurry to 125° C. a clear solution was formed. To the solution a mixture of 57.6 g (0.45 moles) of n-butylacrylate and 6.0 g catalyst (Lupersol ® 575, available from the Lucidol division of Pennwalt Corporation, Philadelphia, Pa.) was added dropwise in 90 min. at 125°–130° C. Ten minutes later, an additional 0.5 g of catalyst, dissolved in 1.0 g of N-methyl pyrrolidone, was added and the reaction was continued for 20 minutes. On cooling, the copolymer precipitated from the solution; it was separated by filtration and purified by washing several times with hot methanol. After drying in a vacuum oven at 80°–90° C. for 4 hours, 23 g of a white powdery solid was obtained. The infrared spectrum (IR) confirmed the expected copolymer structure. The copolymer was practically insoluble in most organic solvents and sparingly soluble in hot dimethyl sulfoxide (DMSO), N-methyl pyrrolidone and tetrahydrofuran (THF).

EXAMPLE 3

Preparation of Butoxymethylated Copolymeric Aminoplast Crosslinking Agent

At room temperature the reactor of Example 2 was charged with 15 g copolymer of Example 2 and 30 g of butylformcel (40% formaldehyde+53% n-butanol+7% water). The temperature of the viscous slurry was raised to 80° C. in 10 minutes. The moderately viscous, hazy solution formed was kept at 85° C. for an additional 15 minutes. The reaction water was removed by azeotropic distillation at 75°–85° C./15–20 inches Hg (32-50 kilo pascals). The slightly hazy, viscous resin solution was diluted with 12 g of n-butanol just before the addition of 0.1 ml 70% nitric acid. For the following 35 minutes the reaction mixture was kept at 70°–75° C. and under vacuum, removing simultaneously 6 ml of distillate. Then the temperature was reduced to 50° C. and the acid catalyst was neutralized by addition of 0.20 ml of 25% caustic solution (pH=7.6). The turbid solution was filtered at 60° C./25 psi (172 kilo pascals) of nitrogen pressure. The "pan solid" content was 44%. For characterization, the resin was separated from the solution by precipitation in n-heptane and dried under vacuum at 50°–60° C. for 5 hrs. The dry polymer was readily soluble in polar solvents, such as chloroform, tetrahydrofuran, and acetone. It was characterized by NMR and IR spectroscopy, HPSEC and thermal analysis. Proton and $^{13}$C NMR suggested the following composition:

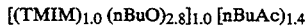

[(TMIM)$_{1.0}$ (nBuO)$_{2.8}$]$_{1.0}$ [nBuAc]$_{1.4}$

The Tg, determined by DSC, was 36±2° C. TGA indicated a 5% weight loss at 187° C. and 10% weight loss at 223° C.

The molecular weights (Mn, Mw) and polydispersity (Mw/Mn=D), determined by HPSEC, were Mn=4075, Mw=11211 and D=2.75.

Abbreviations:
  IR: Infrared
  NMR: Nuclear Magnetic Resonance
  HPSEC: High Performance Size Exclusion Chromatography
  TMIM: TMI/melamine 1:1 adduct
  nBuO: Normal Butoxy Group
  nBuAc: Normal Butyl Acrylate
  Tg: Glass Transition Temperature
  DSC: Differential Scanning Calorimetry
  TGA: Thermal Gravimetric Analysis
  Mn: Number Average Molecular Weight
  Mw: Weight Average Molecular Weight

EXAMPLE 4

The copolymeric aminoplast crosslinking agent of Example 3 was used to prepare the following cured coating systems:
System 1: Acid catalyzed and cured with Joncryl ® 500 acrylic resin, a product of S. C. Johnson and Son, Inc., Racine, Wis.
  Joncryl ® 500/Crosslinker of Example 3: 70/30
  p-TSA, % on TRS: 0.3
  n-Butanol, % on TRS: 15
  % Nonvolatile: 50
System 2: Acid catalyzed but without an active hydrogen-containing polyfunctional material to demonstrate the self-crosslinking ability of the aminoplast.
  Crosslinker of Example 3: 100%
  p-TSA, % on TRS: 0.3
  n-Butanol, % on TRS: 15
  % Nonvolatile: 41
System 3: The crosslinker alone without acid catalyst to demonstrate self-crosslinking ability in the absence of a catalyst.
  Crosslinker of Example 3: 100%
  % Nonvolatile: 37
  Substrate: Bonderite ® 100 CRS (zinc phosphate-treated cold rolled steel)
  Applicator: #46 or #64 Wire Cator
  Cure Schedules: 20' at 100°, 125° and 150° C.
  TRS: Total Resin Solids
  p-TSA: para-Toluenesulfonic Acid
The film properties of the cured films are summarized in Table 1.

TABLE 1

FILM PROPERTIES OF COATINGS PREPARED FROM THE NOVEL COPOLYMERIC AMINOPLAST OF EXAMPLE 3

| | SYSTEM 1 | SYSTEM 2 | SYSTEM 3 |
|---|---|---|---|
| Cure Schedule: 20 min./100° C. | | | |
| Film, mils | 1.4 | 1.3 | 1.3 |
| KHN$_{25}$ | 2.5 | 7.3 | 4.0 |
| MEK Resist | 5/50 | 1/200* | 1/10 |
| *10% removal of film. Cure Schedule: 20 minutes 125° C. | | | |
| Film, mils | 1.2 | 1.2 | 1.3 |
| KHN$_{25}$ | 8.0 | 7.3 | 6.2 |
| MEK Resist | 100/175 | 200+* | 1/200 |
| *Difficult to scratch off after 200 double rubs. Cure Schedule: 20 minutes 150° C. | | | |
| Film, mils | 1.25 | 1.25 | 1.25 |
| KHN$_{25}$ | 9.8 | 10.8 | 7.0 |
| MEK Resist | 200+* | 200+ | 25/200+** |

*Difficult to scratch off after 200 double rubs.
**Heavy scratching; difficult to scratch off after 200 double rubs.

EXAMPLE 5

The procedure of Example 4 was repeated using a different ratio of JONCRYL ® 500 to crosslinker than Example 3, namely, a 50/50 ratio instead of the 70/30 ratio used in Example 4, System 1.

The results are summarized in Table 2 and compared to the results of Example 4.

It is evident from the comparative results in Table 2 that a 50/50 JONCRYL ® 500/Crosslinker ratio produces better cured films under a given set of conditions.

TABLE 2

COMPARISON OF FILM PROPERTIES OF CURED FILMS AT DIFFERENT JONCRYL ® 500 TO CROSSLINKER RATIOS

| Cure Schedule | 20 Min./100° C. | | 20 Min./125° C. | | 20 Min./150° C. | |
|---|---|---|---|---|---|---|
| JONCRYL ® 500/CRSLKR RATIO | 70/30 | 50/50 | 70/30 | 50/50 | 70/30 | 50/50 |
| Film, mils | 1.4 | 1.3 | 1.2 | 1.3 | 1.25 | 1.3 |
| KHN$_{25}$ | 2.5 | 5.5 | 8.0 | 8.5 | 9.8 | 11.0 |
| MEK Resistance | 5/50 | 25/200* | 100/175 | 200+ | 200+** | 200+ |

*Heavy scratching
**Difficult to scratch after 200 double rubs

EXAMPLE 6

An Alternative Method for the Preparation of the Copolymeric Aminoplasts of the Invention A. Preparation of Mixed Alkoxymethylate D Monomeric Polymerizable Aminoplast Monomers A suitable reactor equipped with stirrer, reflux condenser and thermometer was charged with 120 g of butylformcel and the pH adjusted with 20% caustic to 10.1. Then 80 g of the product of Example 1 was added and the temperature of the slurry raised to 85° C.; after eight minutes a clear solution was formed. The temperature was maintained at 85°-90° C. for an additional 30 minutes, then 84 g of n-butanol was added. At 65° C., the pH was adjusted to 2.5 by addition of 0.5 ml of 70% nitric acid and the temperature was maintained for 20 minutes. During the following 35 minutes, 55 ml of distillate was removed at 65°-68° C. and 200 mm Hg (about 27 kilo pascals). The distillate was replaced by adding portionwise to the reactor the same amount of n-butanol. The reaction mixture was cooled to 35° C. and 1.25 ml 20% caustic added to adjust the pH to 9.6. The volatiles were stripped to 96° C./100 mm Hg (about 13 kilo pascals) and 115 g of distillate was collected. At 55° C., 96 g of methanol was charged followed by 0.5 ml of 70% nitric acid at 40° C. (pH=2.1), and the temperature was maintained at 40°-43° C. for 40 minutes. After adjusting the pH to 9.5 with 1.2 ml of 20% caustic, 112 g distillate was removed at 90 mm Hg (12 kilo pascals) up to 95° C. The 120 g of the colorless, moderately viscous resin obtained was diluted with 17 g of toluene and filtered at 80° C. under approximately 2,000 mm Hg pressure of nitrogen gas (about 276 kilo pascals), to give a clear colorless resin having the following characteristics:

HPSEC:
- 81.7% Monomer (High Performance Size Exclusion Chromatography Areas)
- 14.8% Dimer (Areas)
- 3.5% Trimer (Areas)

NMR:
- $CH_3/CH_2 = 0.22$ (ratio)
- $nBu/CH_2 = 0.67$ (ratio)
- $CH_2/Adduct = 3.3$ (ratio)

FREE $CH_2O$: 0.55% (by weight)
FREE METHYLOL: 2.48% (by weight)
SOLIDS:
- Pan = 89.2% (by weight)
- Foil = 95.2% (by weight)

$CH_2O$/ADDUCT: 3.12 (Ratio determined by bound formaldehyde and nitrogen analysis)

B. Copolymerization

The product of Example 6, Part A, when copolymerized with an unsaturated comonomer such as n-butyl acrylate, under the copolymerization conditions described in Example 2 for the copolymerization of the TMI/melamine adduct, should produce mixed alkoxymethylated copolymeric aminoplast crosslinker of the invention.

Although the present invention has been described with reference to certain preferred embodiments, it is apparent that modifications and variations thereof may be made by those skilled in the art without departing from the scope of this invention as defined by the appended claims.

We claim:

1. A copolymer comprising repeating units derived from:
   (i) a monoadduct of isopropenyl-alpha, alpha-dimethylbenzyl isocyanate and an amino compound selected from the group consisting of melamines, guanamines, glycolurils, ureas, N-alkoxyalkylated or alkylolated derivatives thereof, and oligomers thereof; and
   (ii) an ethylenically unsaturated compound capable of copolymerizing with said monoadduct.

2. The copoloymer of claim 1, wherein the isopropenyl-alpha, alpha-dimethylbenzyl isocyanate is selected from the group of isomers consisting of meta-, para-, and a mixture thereof.

3. The copolymer of claim 2, wherein the isopropenyl-alpha, alpha-dimethylbenzyl isocyanate is the meta-isomer.

4. The copolymer of claim 1, wherein the amino compound is selected from the group consisting of melamine, an alkoxyalkylated melamine, an alkylolated melamine and mixtures thereof.

5. The copolymer of claim 1, wherein the ethylenically unsaturated compound is selected from the group consisting of vinyl acetate, styrene, acrylic and methacrylic esters, acrylic and methacrylic nitriles, acrylic and methacrylic amides, vinyl chloride, vinylidene chloride, fumarate and maleate esters, cinnamate esters, maleic anhydride, maleimide, N-methyl maleimide, N-phenyl maleimide, and a mixture thereof.

6. The copolymer of claim 1, possessing a weight average molecular weight of from about 500 to about 20,000.

7. A copolymer comprising a plurality of the same or different segments represented by the formula:

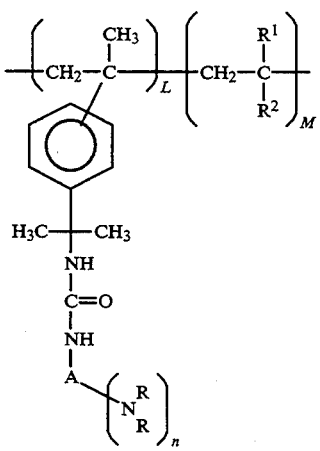

wherein
L and M are the same or different integers, each independently having a value of at least 1;

A is a core of an amino compound selected from the group consisting of melamines, guanamines, glycolurils, ureas, N-derivatives thereof, and oligomers, thereof;

each R is independently selected from H, an alkylol group and an alkoxyalkyl group;

$R^1$ and $R^2$ are the same or different and independently selected from the group consisting of hydrogen, cyano, halo, alkoxy, acetoxy, acyl, aminocarbonyl, N-alkylaminocarbonyl, N,N-dialkylaminocarbonyl, aryl, alkoxycarbonyl of 1 to 20 carbon atoms, aryloxycarbonyl of 6 to 20 carbon atoms, and aralkyloxycarbonyl of 7 to 20 carbon atoms; and n is at least one.

8. The copolymer of claim 7, wherein each R group is independently selected from H, a methylol group and an alkoxymethyl group having from 1 to 6 carbon atoms in the alkoxy group.

9. The copolymer of claim 8, wherein each R group is independently selected from the a methylol group and an alkoxymethyl group having from 1 to 6 carbon atoms in the alkoxy group.

10. The copolymer of claim 9, wherein substantially all of the R groups are alkoxymethyl groups having from 1 to 6 carbon atoms in the alkoxy group.

11. The copolymer of claim 7, wherein A is the core of a melamine, and each R group is independently selected from H, a methylol group and an alkoxymethyl group having from 1 to 6 carbon atoms in the alkoxy group.

12. The copolymer of claim 7, possessing a weight average molecular weight of from about 500 to about 20,000.

13. A process for preparing a copolymer comprising repeating units derived from:
(i) a monoadduct of isopropenyl-alpha, alpha-dimethylbenzyl isocyanate and an amino compound selected from the group consisting of melamines, guanamines, glycolurils, N-alkoxyalkylated or alkylolated derivatives thereof, and oligomers thereof; and
(ii) an ethylenically unsaturated compound capable of copolymerizing with said monoadduct,
comprising the steps of:

(a) dissolving, in a liquid medium, the monoadduct to form a solution;
(b) adding to the solution (i) an unsaturated comonomer and (ii) a free radical initiator, and
(c) maintaining the reaction mixture at a temperature and for a length of time sufficient to copolymerize at least 90 weight percent of the adduct and the comonomer reactants.

14. The process of claim 13, further comprising the step of (d) contacting the product of step (c) with 1 to 30 moles of formaldehyde per mole of monoadduct.

15. The process of claim 14, further comprising the step of (e) contacting the product of step (d) with 1 to 30 moles of an alcohol per mole of monoadduct, under acidic conditions.

16. A curable composition comprising a polyfunctional active hydrogen-containing material, and a copolymer comprising a plurality of the same or different segments represented by the formula:

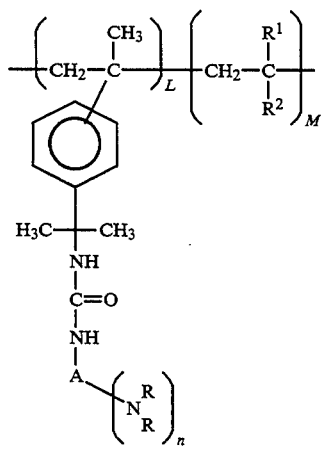

wherein
L and M are the same or different integers, each independently having a value of at least 1;

A is a core of an amino compound selected from the group consisting of melamines, guanamines, glycolurils, ureas, N-derivatives thereof and oligomers thereof;

each R is independently selected from H, an alkylol group and an alkoxyalkyl group, whereby at least a portion of the R groups are selected from an alkylol group and an alkoxyalkyl group;

$R^1$ and $R^2$ are the same or different and independently selected from the group consisting of hydrogen, cyano, halo, alkoxy, acetoxy, acyl, aminocarbonyl, N-alkylaminocarbonyl, N,N-dialkylaminocarbonyl, aryl, alkoxycarbonyl of 1 to 20 carbon atoms, aryloxycarbonyl of 6 to 20 carbon atoms, and aralkyloxycarbonyl of 7 to 20 carbon atoms; and n is at least one.

17. A method for coating a substrate by contacting a substrate with a curable composition and thereafter curing, wherein the curable composition comprises a copolymer comprising a plurality of the same or different segments represented by the formula:

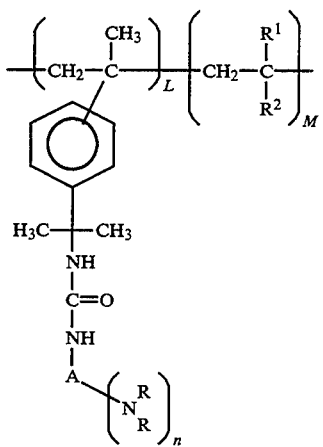

wherein

L and M are the same or different integers, each independently having a value of at least 1;

A is a core of an amino compound selected from the group consisting of melamines, guanamines, glycolurils, ureas, N-derivatives thereof, and oligomers thereof;

each R is independently selected from H, an alkylol group and an alkoxyalkyl group, whereby at least a portion of the R groups are selected from an alkylol group and an alkoxyalkyl group;

$R^1$ and $R^2$ are the same or different and independently selected from the group consisting of hydrogen, cyano, halo, alkoxy, acetoxy, acyl, aminocarbonyl, N-alkylaminocarbonyl, N,N-dialkylaminocarbonyl, aryl, alkoxycarbonyl of 1 to 20 carbon atoms, aryloxycarbonyl of 6 to 20 carbon atoms, and aralkyloxycarbonyl of 7 to 20 carbon atoms; and n is at least one.

18. The method of claim 17, wherein the curable composition further comprises a polyfunctional active hydrogen-containing material.

19. The process of claim 13, wherein the amino compound is selected from the group consisting of melamine, an alkoxyalkylated melamine, an akylolated melamine and mixtures thereof.

20. The curable composition of claim 16, wherein each R group is independently selected from H, a methylol group and an alkoxymethyl group having from 1 to 6 carbon atoms in the alkoxy group.

21. The curable composition of claim 20, wherein each R group is independently selected from a methylol group and an alkoxymethyl group having from 1 to 6 carbon atoms in the alkoxy group.

22. The curable composition of claim 21, wherein substantially all of the R groups are alkoxymethyl groups having from 1 to 6 carbon atoms in the alkoxy group.

23. The curable composition of claim 16, wherein A is the core of a melamine, and each R group is independently selected from H, a methylol group and an alkoxymethyl group having from 1 to 6 carbon atoms in the alkoxy group.

24. The curable composition of claim 16, wherein the copolymer possesses a weight average molecular weight of from about 500 to about 20,000.

25. The method of claim 17, wherein each R group is independently selected from H, a methylol group and an alkoxymethyl group having from 1 to 6 carbon atoms in the alkoxy group.

26. The method of claim 24, wherein each R group is independently selected from a methylol group and an alkoxymethyl group having from 1 to 6 carbon atoms in the alkoxy group.

27. The method of claim 26, wherein substantially all of the R group are alkoxymethyl groups having from 1 to 6 carbon atoms in the alkoxy group.

28. The method of claim 17, wherein A is the core of a melamine, and each R group is independently selected from H, a methylol group and an alkoxymethyl group having from 1 to 6 carbon atoms in the alkoxy group.

29. The method of claim 17, when the copolymer possesses a weight average molecular weight of from about 500 to about 20,000.

* * * * *